(12) United States Patent
Markovitz et al.

(10) Patent No.: US 11,969,254 B2
(45) Date of Patent: Apr. 30, 2024

(54) SYSTEM AND METHOD FOR CARDIAC MAPPING

(71) Applicant: St. Jude Medical, Cardiology Division, Inc., St. Paul, MN (US)

(72) Inventors: Craig Markovitz, Mahtomedi, MN (US); Jan O. Mangual-Soto, Rho (IT); Chunlan Jiang, Northridge, CA (US); Louis-Philippe Richer, Montreal (CA); Cyrille Casset, Saint Selve (FR)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 438 days.

(21) Appl. No.: 17/438,023

(22) PCT Filed: Feb. 11, 2020

(86) PCT No.: PCT/US2020/017666
§ 371 (c)(1),
(2) Date: Sep. 10, 2021

(87) PCT Pub. No.: WO2020/185339
PCT Pub. Date: Sep. 17, 2020

(65) Prior Publication Data
US 2022/0142553 A1    May 12, 2022

Related U.S. Application Data

(60) Provisional application No. 62/817,224, filed on Mar. 12, 2019.

(51) Int. Cl.
*A61B 5/36* (2021.01)
*A61B 5/339* (2021.01)
(Continued)

(52) U.S. Cl.
CPC .............. *A61B 5/367* (2021.01); *A61B 5/339* (2021.01); *A61B 5/352* (2021.01)

(58) Field of Classification Search
None
See application file for complete search history.

(56) References Cited

U.S. PATENT DOCUMENTS 5,697,377 A   12/1997  Wittkampf
5,983,126 A   11/1999  Wittkampf
(Continued)

OTHER PUBLICATIONS

International Preliminary Report on Patentability Chapter I received for International PCT Application Serial No. PCT/US2020/017666 dated Sep. 23, 2021, 9 pages.
(Continued)

*Primary Examiner* — Ankit D Tejani
(74) *Attorney, Agent, or Firm* — Wiley Rein LLP

(57) ABSTRACT

When generating anatomical maps (e.g., anatomical geometries and/or electrophysiology maps), it can be desirable to analyze whether or not a collected data point was collected from a region of interest. During an electrophysiology study, for example, an electroanatomical mapping system collects electrophysiology data points, each including an electrogram signal. By defining both a window of interest and a window of exclusion within the electrogram signal, the electroanatomical mapping system can analyze collected data points to determine whether or not they should be included in a map. In particular, the electroanatomical mapping system can compare the electrophysiology signal within the window of interest and the window of exclusion with respect to at least one signal parameter and add the data point to the map if the comparison satisfies at least one corresponding inclusion criterion. Applicable signal parameters include maximum peak-to-peak voltage, conduction velocity, and electrogram morphology.

20 Claims, 6 Drawing Sheets

(51) Int. Cl.
*A61B 5/352* (2021.01)
*A61B 5/367* (2021.01)

(56) References Cited

U.S. PATENT DOCUMENTS

| | | | |
|---|---|---|---|
| 6,640,119 | B1 | 10/2003 | Budd et al. |
| 6,728,562 | B1 | 4/2004 | Budd et al. |
| 6,939,309 | B1 | 9/2005 | Beatty et al. |
| 6,947,785 | B1 | 9/2005 | Beatty et al. |
| 6,978,168 | B2 | 12/2005 | Beatty et al. |
| 6,990,370 | B1 | 1/2006 | Beatty et al. |
| 7,263,397 | B2 | 8/2007 | Hauck et al. |
| 7,885,707 | B2 | 2/2011 | Hauck |
| 10,758,137 | B2 | 9/2020 | Deno et al. |
| 2013/0304407 | A1* | 11/2013 | George ............ A61B 5/7246 702/72 |
| 2015/0057507 | A1 | 2/2015 | Koyrakh et al. |
| 2015/0119738 | A1* | 4/2015 | Deno ............ A61B 5/316 600/509 |
| 2017/0071493 | A1 | 3/2017 | Yang et al. |
| 2018/0132743 | A1 | 5/2018 | Markovitz |
| 2018/0199847 | A1 | 7/2018 | Markovitz et al. |

OTHER PUBLICATIONS

Jude, St., et al., "EnSite(TM) AutoMap Module Instruction for Use", Retrieved from: URL: https://manuals.sjm.com/~/media/manuals/product-manual-pdfs/1/1/1120aced-5475-4238-a695-54a9a7befd3b.pdf, 1200 pages, Oct. 31, 2016.

Jude, St., et al., "EnSite Precision(TM) Cardiac Mapping System Model EE3000 Instructions for Use U.S. Edition", Retrieved from: URL: https://manuals.sjm.com/~/media/manuals/product-manual-pdfs/f/5/f5a336fa-f714-46ba-808c-528cf101e848.pdf, 1200 pages, Jan. 1, 2016.

* cited by examiner

SYSTEM AND METHOD FOR CARDIAC MAPPING

CROSS-REFERENCE TO RELATED APPLICATIONS

This application claims the benefit of U.S. provisional application No. 62/817,224, filed 12 Mar. 2019, which is hereby incorporated by reference as though fully set forth herein.

BACKGROUND

The present disclosure relates generally to cardiac mapping, such as may be performed in cardiac diagnostic and therapeutic procedures. In particular, the present disclosure relates to systems, apparatuses, and methods for generating cardiac geometry and/or electrophysiology maps from data collected by a roving electrophysiology probe, such as a high density ("HD") grid catheter or other multi-electrode device.

Cardiac mapping, including the generation of cardiac geometries and electrocardiographic mapping, is a part of numerous cardiac diagnostic and therapeutic procedures. As the complexity of such procedures increases, however, the geometries and electrophysiology maps utilized must increase in quality, in density, and in the rapidity and ease with which they can be generated.

It is known to use a multi-electrode catheter, such as an HD grid catheter, to gather data points used in the creation of cardiac geometries and/or electrophysiology maps. During an electrophysiology study, however, the catheter (or a portion thereof) may move into a region other than the region of interest. For instance, when mapping the left atrium, the catheter may inadvertently pass through the mitral valve into the left ventricle.

BRIEF SUMMARY

Disclosed herein is a method of generating a map of a portion of a patient's anatomy. The method includes the steps of: receiving, at an electroanatomical mapping system, an electrophysiology data point, the electrophysiology data point including an electrogram signal; receiving, at the electroanatomical mapping system, a definition of a window of interest within the electrogram signal and a definition of a window of exclusion within the electrogram signal (e.g., a QRS complex); and the electroanatomical mapping system adding the electrophysiology data point to the map of the portion of the patient's anatomy when a maximum peak-to-peak voltage of the electrogram signal within the window of interest exceeds a maximum peak-to-peak voltage of the electrogram signal within the window of exclusion. The method can also include the electroanatomical mapping system adding the electrophysiology data point to the map of the portion of the patient's anatomy when the maximum peak-to-peak voltage of the electrogram signal within the window of interest does not exceed the maximum peak-to-peak voltage of the electrogram signal within the window of exclusion and the maximum peak-to-peak voltage of the electrogram signal within the window of exclusion does not exceed a preset threshold voltage.

The foregoing method can be applied to generate an electrophysiology map. Alternatively or additionally, the foregoing method can be applied to generate a geometry.

Aspects of the disclosure also relate to outputting a graphical representation of the map of the portion of the patient's anatomy.

In another embodiment, the instant disclosure provides a method of generating a map of a portion of a patient's anatomy, including: receiving, at the electroanatomical mapping system, an electrophysiology data point, the electrophysiology data point including an electrogram signal; receiving, at an electroanatomical mapping system, a definition of a window of interest within the electrogram signal and a definition of a window of exclusion within the electrogram signal; and the electroanatomical mapping system adding the electrophysiology data point to the map of the portion of the patient's anatomy when a comparison of the window of interest to the window of exclusion with respect to at least one signal parameter satisfies at least one corresponding inclusion criterion. Optionally, the electroanatomical mapping system can add the electrophysiology data point to an alternative map of the portion of the patient's anatomy when the comparison of the window of interest to the window of exclusion with respect to the at least one signal parameter does not satisfy the at least one corresponding inclusion criterion.

The at least one signal parameter can, for example, be maximum peak-to-peak voltage, and the at least one corresponding inclusion criterion can be a maximum peak-to-peak voltage of the electrogram signal within the window of interest exceeding a maximum peak-to-peak voltage of the electrogram signal within the window of exclusion. The at least one corresponding inclusion criterion can also be: a maximum peak-to-peak voltage of the electrogram signal within the window of interest not exceeding a maximum peak-to-peak voltage of the electrogram signal within the window of exclusion; and the maximum peak-to-peak voltage of the electrogram signal within the window of exclusion interval not exceeding a preset threshold voltage.

In other embodiments of the disclosure, the at least one signal parameter can be electrogram morphology and/or conduction velocity.

Also disclosed herein is an electroanatomical mapping system for generating a map of a portion of a patient's anatomy. The system includes an inclusion processor configured to: receive as input an electrophysiology data point including an electrogram signal; receive as input a definition of a window of interest within the electrogram signal and a definition of a window of exclusion within the electrogram signal; compare the window of interest to the window of exclusion with respect to at least one signal parameter; and add the electrophysiology data point to the map of the portion of the patient's anatomy when the comparison of the window of interest to the window of exclusion satisfies at least one corresponding inclusion criterion. The system can also include a mapping processor configured to output a graphical representation of the map of the portion of the patient's anatomy. The map of the portion of the patient's anatomy can include a cardiac geometry and/or an electrophysiology map.

In aspects of the disclosure, the at least one signal parameter can be maximum peak-to-peak voltage and the at least one corresponding inclusion criterion can be a maximum peak-to-peak voltage of the electrogram signal within the window of interest exceeding a maximum peak-to-peak voltage of the electrogram signal within the window of exclusion.

In other aspects of the disclosure, the at least one signal parameter can be maximum peak-to-peak voltage and the at least one corresponding inclusion criterion can be a maximum peak-to-peak voltage of the electrogram signal within the window of interest not exceeding a maximum peak-to-peak voltage of the electrogram signal within the window of exclusion; and the maximum peak-to-peak voltage of the electrogram signal within the window of exclusion interval not exceeding a preset threshold voltage.

The foregoing and other aspects, features, details, utilities, and advantages of the present invention will be apparent from reading the following description and claims, and from reviewing the accompanying drawings.

While multiple embodiments are disclosed, still other embodiments of the present disclosure will become apparent to those skilled in the art from the following detailed description, which shows and describes illustrative embodiments. Accordingly, the drawings and detailed description are to be regarded as illustrative in nature and not restrictive.

DETAILED DESCRIPTION

The instant disclosure provides systems, apparatuses, and methods for generating anatomical maps, such as surface geometries (anatomical models) and electrophysiology maps. For purposes of illustration, aspects of the disclosure will be described with reference to cardiac electrophysiology procedures. More specifically, aspects of the disclosure will be described in the context of the creation of cardiac geometries and cardiac electrophysiology maps from electrophysiology data points collected using a high density (HD) grid catheter, such as the Advisor™ HD grid mapping catheter from Abbott Laboratories (Abbott Park, Illinois), in conjunction with an electroanatomical mapping system, such as the EnSite Precision™ cardiac mapping system, also from Abbott Laboratories. Even more specifically, aspects of the disclosure will be described with reference to atrial mapping. Those of ordinary skill in the art will understand, however, how to apply the teachings herein to good advantage in other contexts and/or with respect to other devices.

Figure 1:
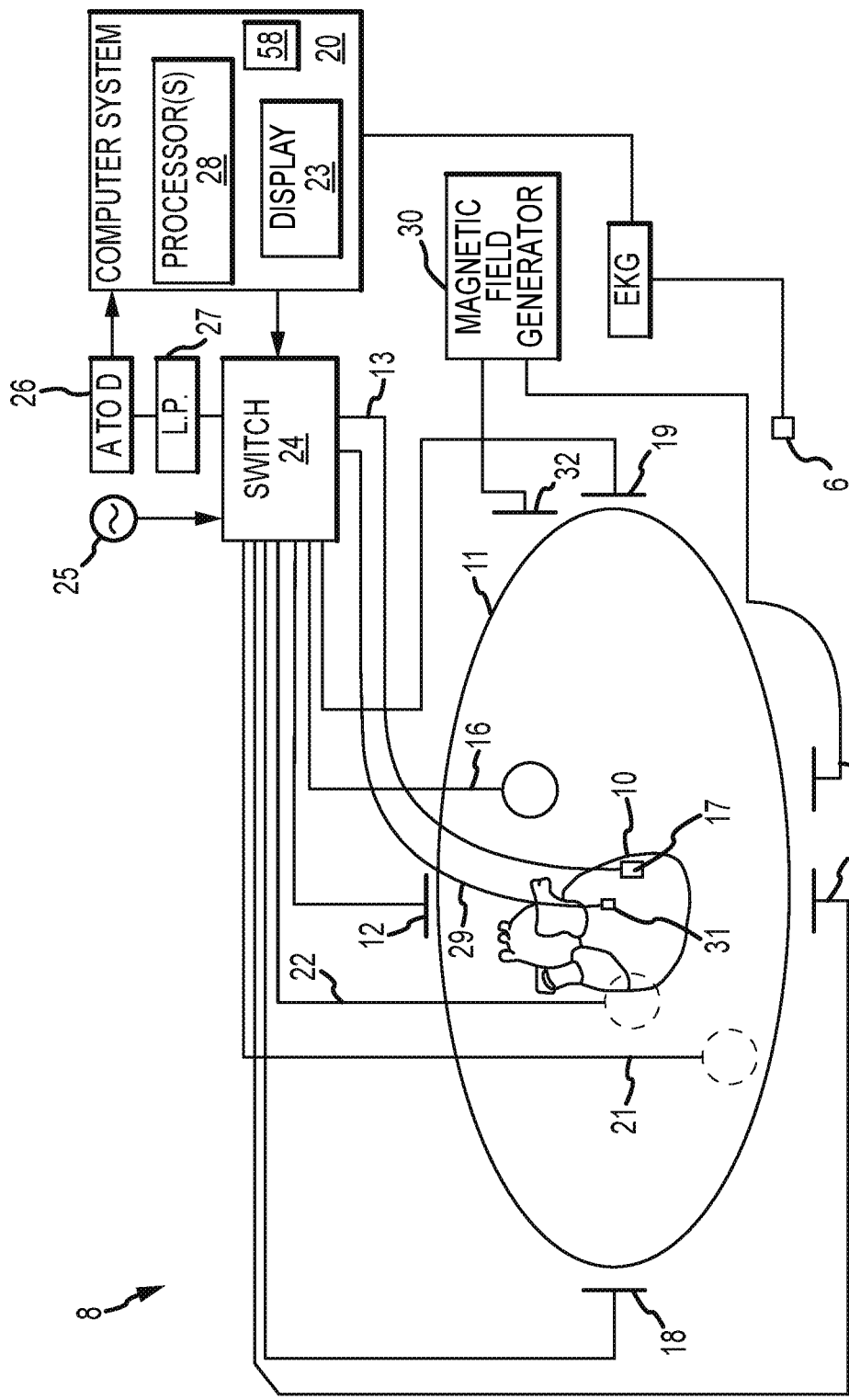
FIG. 1 is a schematic diagram of an exemplary electroanatomical mapping system.

FIG. 1 shows a schematic diagram of an exemplary electroanatomical mapping system 8 for conducting cardiac electrophysiology studies by navigating a cardiac catheter and measuring electrical activity occurring in a heart 10 of a patient 11 and three-dimensionally mapping the electrical activity and/or information related to or representative of the electrical activity so measured. System 8 can be used, for example, to create an anatomical model of the patient's heart 10 using one or more electrodes. System 8 can also be used to measure electrophysiology data at a plurality of points along a cardiac surface and store the measured data in association with location information for each measurement point at which the electrophysiology data was measured, for example to create a diagnostic data map of the patient's heart 10.

As one of ordinary skill in the art will recognize, system 8 determines the location, and in some aspects the orientation, of objects, typically within a three-dimensional space, and expresses those locations as position information determined relative to at least one reference.

For simplicity of illustration, the patient 11 is depicted schematically as an oval. In the embodiment shown in FIG. 1, three sets of surface electrodes (e.g., patch electrodes) are shown applied to a surface of the patient 11, defining three generally orthogonal axes, referred to herein as an x-axis, a y-axis, and a z-axis. In other embodiments the electrodes could be positioned in other arrangements, for example multiple electrodes on a particular body surface. As a further alternative, the electrodes do not need to be on the body surface, but could be positioned internally to the body.

In FIG. 1, the x-axis surface electrodes 12, 14 are applied to the patient along a first axis, such as on the lateral sides of the thorax region of the patient (e.g., applied to the patient's skin underneath each arm) and may be referred to as the Left and Right electrodes. The y-axis electrodes 18, 19 are applied to the patient along a second axis generally orthogonal to the x-axis, such as along the inner thigh and neck regions of the patient, and may be referred to as the Left Leg and Neck electrodes. The z-axis electrodes 16, 22 are applied along a third axis generally orthogonal to both the x-axis and the y-axis, such as along the sternum and spine of the patient in the thorax region, and may be referred to as the Chest and Back electrodes. The heart 10 lies between these pairs of surface electrodes 12/14, 18/19, and 16/22.

An additional surface reference electrode (e.g., a "belly patch") 21 provides a reference and/or ground electrode for the system 8. The belly patch electrode 21 may be an alternative to a fixed intra-cardiac electrode 31, described in further detail below. It should also be appreciated that, in addition, the patient 11 may have most or all of the conventional electrocardiogram ("ECG" or "EKG") system leads in place. In certain embodiments, for example, a standard set of 12 ECG leads may be utilized for sensing electrocardiograms on the patient's heart 10. This ECG information is available to the system 8 (e.g., it can be provided as input to computer system 20). Insofar as ECG leads are well understood, and for the sake of clarity in the figures, only a single lead 6 and its connection to computer 20 is illustrated in FIG. 1.

A representative catheter 13 having at least one electrode 17 is also shown. This representative catheter electrode 17 is referred to as the "roving electrode," "moving electrode," or "measurement electrode" throughout the specification. Typically, multiple electrodes 17 on catheter 13, or on multiple such catheters, will be used. In one embodiment, for example, the system 8 may comprise sixty-four electrodes on twelve catheters disposed within the heart and/or vasculature of the patient. In other embodiments, system 8 may utilize a single catheter that includes multiple (e.g., eight) splines, each of which in turn includes multiple (e.g., eight) electrodes.

Figure 2:
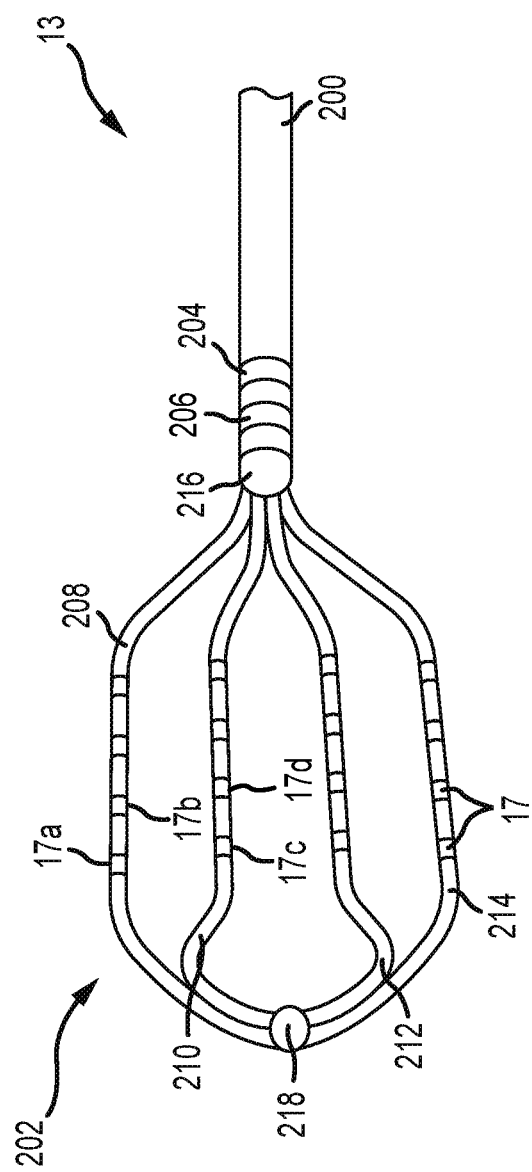
FIG. 2 depicts an exemplary catheter that can be used in connection with aspects of the instant disclosure.

The foregoing embodiments are merely exemplary, however, and any number of electrodes and/or catheters may be used. For example, for purposes of this disclosure, a segment of an exemplary multi-electrode catheter, and in particular an HD grid catheter, is shown in FIG. 2. HD grid catheter 13 includes a catheter body 200 coupled to a paddle 202. Catheter body 200 can further include first and second body electrodes 204, 206, respectively. Paddle 202 can include a first spline 208, a second spline 210, a third spline 212, and a fourth spline 214, which are coupled to catheter body 200 by a proximal coupler 216 and to each other by a distal coupler 218. In one embodiment, first spline 208 and fourth spline 214 can be one continuous segment and second spline 210 and third spline 212 can be another continuous segment. In other embodiments, the various splines 208, 210, 212, 214 can be separate segments coupled to each other (e.g., by proximal and distal couplers 216, 218, respectively). It should be understood that HD catheter 13 can include any number of splines; the four-spline arrangement shown in FIG. 2 is merely exemplary.

As described above, splines 208, 210, 212, 214 can include any number of electrodes 17; in FIG. 2, sixteen electrodes 17 are shown arranged in a four-by-four array. It should also be understood that electrodes 17 can be evenly and/or unevenly spaced, as measured both along and between splines 208, 210, 212, 214.

Catheter 13 (or multiple such catheters) are typically introduced into the heart and/or vasculature of the patient via one or more introducers and using familiar procedures. Indeed, various approaches to introduce catheter 13 into a patient's heart, such as transseptal approaches, will be familiar to those of ordinary skill in the art, and therefore need not be further described herein.

Since each electrode 17 lies within the patient, location data may be collected simultaneously for each electrode 17 by system 8. Similarly, each electrode 17 can be used to gather electrophysiological data from the cardiac surface (e.g., surface electrograms). The ordinarily skilled artisan will be familiar with various modalities for the acquisition and processing of electrophysiology data points (including, for example, both contact and non-contact electrophysiological mapping), such that further discussion thereof is not necessary to the understanding of the techniques disclosed herein. Likewise, various techniques familiar in the art can be used to generate a graphical representation of a cardiac geometry and/or of cardiac electrical activity from the plurality of electrophysiology data points. Moreover, insofar as the ordinarily skilled artisan will appreciate how to create electrophysiology maps from electrophysiology data points, the aspects thereof will only be described herein to the extent necessary to understand the present disclosure.

Returning now to FIG. 1, in some embodiments, an optional fixed reference electrode 31 (e.g., attached to a wall of the heart 10) is shown on a second catheter 29. For calibration purposes, this electrode 31 may be stationary (e.g., attached to or near the wall of the heart) or disposed in a fixed spatial relationship with the roving electrodes (e.g., electrodes 17), and thus may be referred to as a "navigational reference" or "local reference." The fixed reference electrode 31 may be used in addition or alternatively to the surface reference electrode 21 described above. In many instances, a coronary sinus electrode or other fixed electrode in the heart 10 can be used as a reference for measuring voltages and displacements; that is, as described below, fixed reference electrode 31 may define the origin of a coordinate system.

Each surface electrode is coupled to a multiplex switch 24, and the pairs of surface electrodes are selected by software running on a computer 20, which couples the surface electrodes to a signal generator 25. Alternately, switch 24 may be eliminated and multiple (e.g., three) instances of signal generator 25 may be provided, one for each measurement axis (that is, each surface electrode pairing).

The computer 20 may comprise, for example, a conventional general-purpose computer, a special-purpose computer, a distributed computer, or any other type of computer. The computer 20 may comprise one or more processors 28, such as a single central processing unit ("CPU"), or a plurality of processing units, commonly referred to as a parallel processing environment, which may execute instructions to practice the various aspects described herein.

Generally, three nominally orthogonal electric fields are generated by a series of driven and sensed electric dipoles (e.g., surface electrode pairs 12/14, 18/19, and 16/22) in order to realize catheter navigation in a biological conductor. Alternatively, these orthogonal fields can be decomposed and any pairs of surface electrodes can be driven as dipoles to provide effective electrode triangulation. Likewise, the electrodes 12, 14, 18, 19, 16, and 22 (or any number of electrodes) could be positioned in any other effective arrangement for driving a current to or sensing a current from an electrode in the heart. For example, multiple electrodes could be placed on the back, sides, and/or belly of patient 11. Additionally, such non-orthogonal methodologies add to the flexibility of the system. For any desired axis, the potentials measured across the roving electrodes resulting from a predetermined set of drive (source-sink) configurations may be combined algebraically to yield the same effective potential as would be obtained by simply driving a uniform current along the orthogonal axes.

Thus, any two of the surface electrodes 12, 14, 16, 18, 19, 22 may be selected as a dipole source and drain with respect to a ground reference, such as belly patch 21, while the unexcited electrodes measure voltage with respect to the ground reference. The roving electrodes 17 placed in the heart 10 are exposed to the field from a current pulse and are measured with respect to ground, such as belly patch 21. In practice the catheters within the heart 10 may contain more or fewer electrodes than the sixteen shown, and each electrode potential may be measured. As previously noted, at least one electrode may be fixed to the interior surface of the heart to form a fixed reference electrode 31, which is also measured with respect to ground, such as belly patch 21, and which may be defined as the origin of the coordinate system relative to which system 8 measures positions. Data sets from each of the surface electrodes, the internal electrodes, and the virtual electrodes may all be used to determine the location of the roving electrodes 17 within heart 10.

The measured voltages may be used by system 8 to determine the location in three-dimensional space of the electrodes inside the heart, such as roving electrodes 17 relative to a reference location, such as reference electrode 31. That is, the voltages measured at reference electrode 31 may be used to define the origin of a coordinate system, while the voltages measured at roving electrodes 17 may be used to express the location of roving electrodes 17 relative to the origin. In some embodiments, the coordinate system is a three-dimensional (x, y, z) Cartesian coordinate system, although other coordinate systems, such as polar, spherical, and cylindrical coordinate systems, are contemplated.

As should be clear from the foregoing discussion, the data used to determine the location of the electrode(s) within the heart is measured while the surface electrode pairs impress an electric field on the heart. The electrode data may also be used to create a respiration compensation value used to improve the raw location data for the electrode locations as described, for example, in U.S. Pat. No. 7,263,397, which is hereby incorporated herein by reference in its entirety. The electrode data may also be used to compensate for changes in the impedance of the body of the patient as described, for example, in U.S. Pat. No. 7,885,707, which is also incorporated herein by reference in its entirety.

Therefore, in one representative embodiment, system 8 first selects a set of surface electrodes and then drives them with current pulses. While the current pulses are being delivered, electrical activity, such as the voltages measured with at least one of the remaining surface electrodes and in vivo electrodes, is measured and stored. Compensation for artifacts, such as respiration and/or impedance shifting, may be performed as indicated above.

In aspects of the disclosure, system 8 can be a hybrid system that incorporates both impedance-based (e.g., as described above) and magnetic-based localization capabilities. Thus, for example, system 8 can also include a magnetic source 30, which is coupled to one or more magnetic field generators. In the interest of clarity, only two magnetic field generators 32 and 33 are depicted in FIG. 1, but it should be understood that additional magnetic field generators (e.g., a total of six magnetic field generators, defining three generally orthogonal axes analogous to those defined by patch electrodes 12, 14, 16, 18, 19, and 22) can be used without departing from the scope of the present teachings. Likewise, those of ordinary skill in the art will appreciate that, for purposes of localizing catheter 13 within the magnetic fields so generated, can include one or more magnetic localization sensors (e.g., coils).

In some embodiments, system 8 is the EnSite™ Velocity™ or EnSite Precision™ cardiac mapping and visualization system of Abbott Laboratories. Other localization systems, however, may be used in connection with the present teachings, including for example the RHYTHMIA HDX™ mapping system of Boston Scientific Corporation (Marlborough, Massachusetts), the CARTO navigation and location system of Biosense Webster, Inc. (Irvine, California), the AURORA® system of Northern Digital Inc. (Waterloo, Ontario), Sterotaxis, Inc.'s NIOBE® Magnetic Navigation System (St. Louis, Missouri), as well as MediGuide™ Technology from Abbott Laboratories.

The localization and mapping systems described in the following patents (all of which are hereby incorporated by reference in their entireties) can also be used with the present invention: U.S. Pat. Nos. 6,990,370; 6,978,168; 6,947,785; 6,939,309; 6,728,562; 6,640,119; 5,983,126; and 5,697,377.

Aspects of the disclosure relate to generating anatomical maps (that is, maps of portions of a patient's anatomy, such as cardiac geometries and/or electrophysiology maps). Graphical representations of such maps can also be output, for example on display 23. System 8 can therefore include an inclusion module 58 that can be used to generate an anatomical map, and which may incorporate a mapping module to allow for graphical output thereof (e.g., to display 23).

Figure 3:
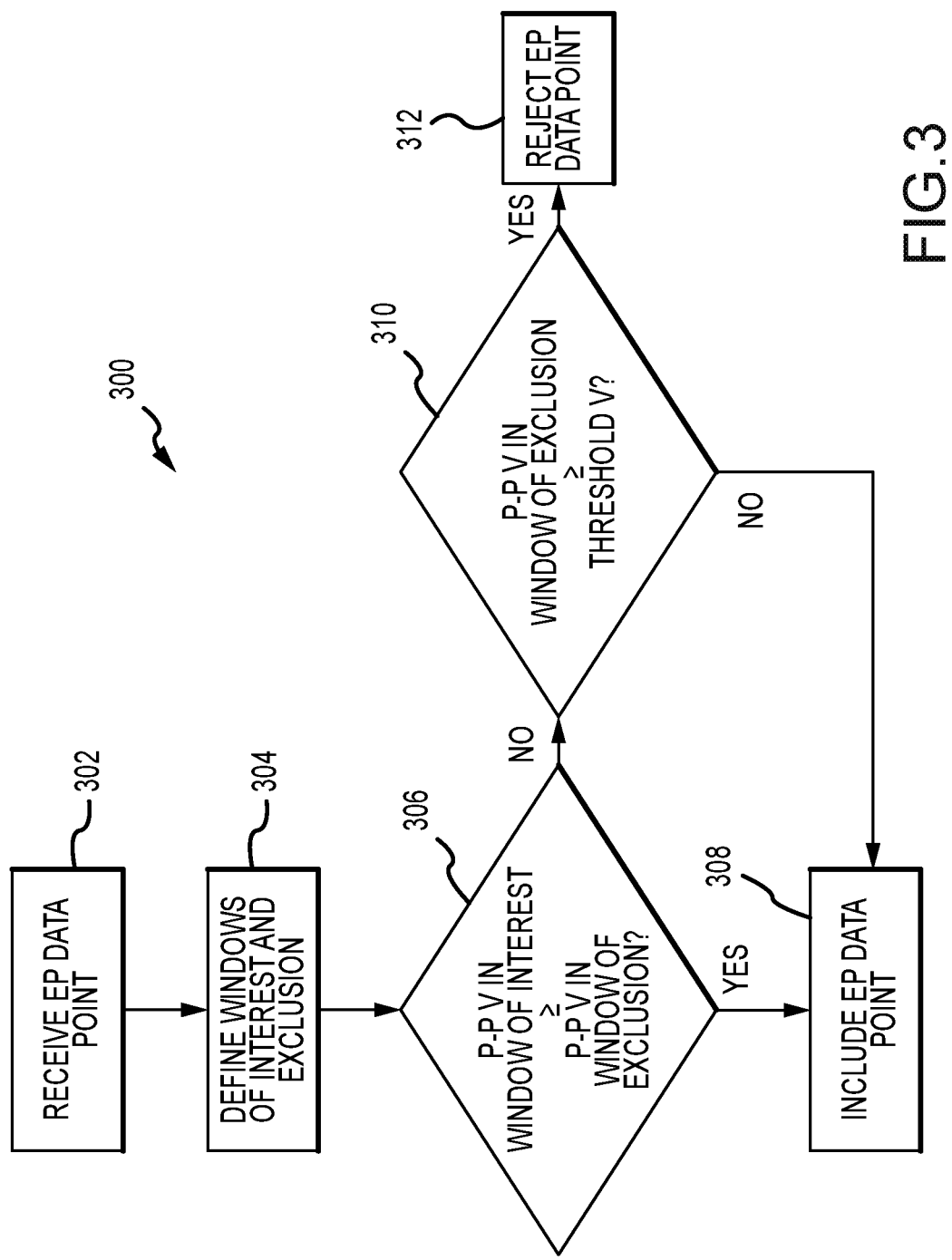
FIG. 3 is a flowchart of representative steps that can be carried out according to exemplary embodiments disclosed herein.

One exemplary method according to the present teachings will be explained with reference to the flowchart 300 of representative steps presented as FIG. 3. In some embodiments, for example, flowchart 300 may represent several exemplary steps that can be carried out by electroanatomical mapping system 8 of FIG. 1 (e.g., by processor 28 and/or inclusion module 58). It should be understood that the representative steps described below can be either hardware- or software-implemented. For the sake of explanation, the term "signal processor" is used herein to describe both hardware- and software-based implementations of the teachings herein.

In block 302, system 8 receives an electrophysiology data point from electrodes 17 carried by catheter 13. For purposes of easy reference in this description, FIG. 4A provides alphanumeric labels for electrodes 17.

As those of ordinary skill in the art will recognize, any two neighboring electrodes 17 define a bipole. Thus, the 16 electrodes 17 on catheter 13 define a total of 42 bipoles—12 along splines (e.g., between electrodes 17a and 17b, or between electrodes 17c and 17d), 12 across splines (e.g., between electrodes 17a and 17c, or between electrodes 17b and 17d), and 18 diagonally between splines (e.g., between electrodes 17a and 17d, or between electrodes 17b and 17c).

Figure 4B:
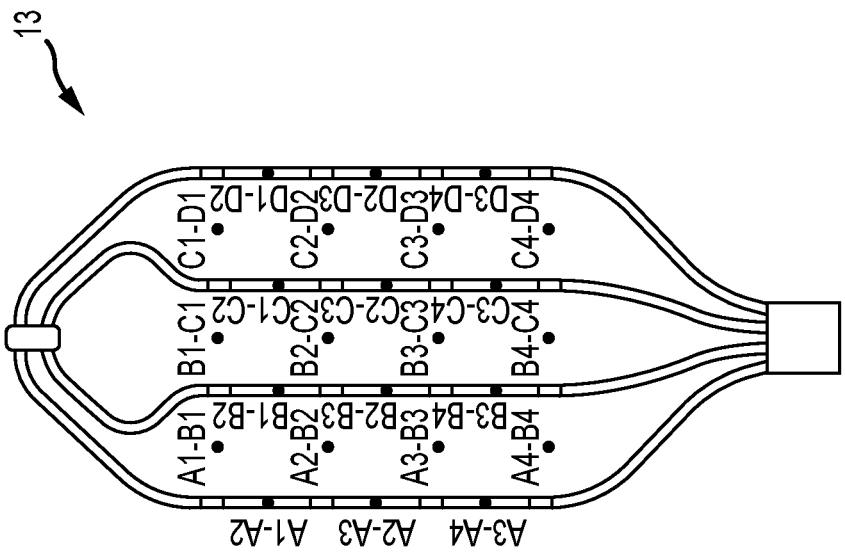
FIGS. 4A and 4B provide alphanumeric labeling conventions for electrodes carried by a multi-electrode catheter and the bipoles associated therewith.
Figure 4A:
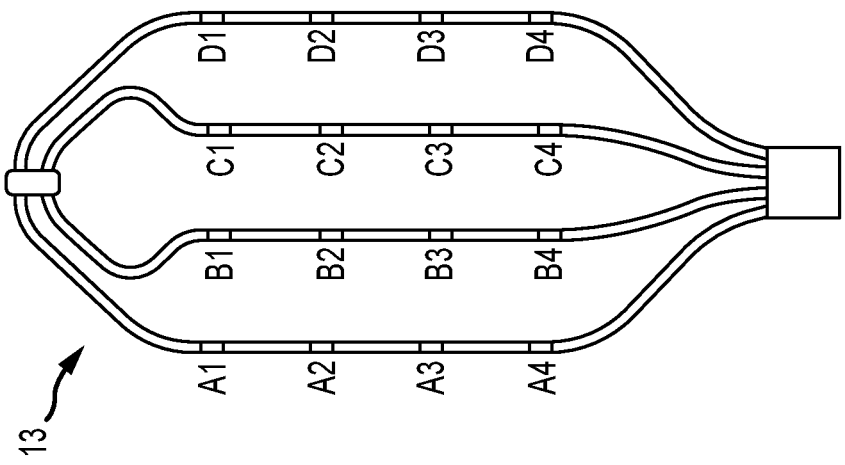

For ease of reference in this description, FIG. 4B provides alphanumeric labels for the along- and across-spline bipoles. FIG. 4B omits alphanumeric labels for the diagonal bipoles, but this is only for the sake of clarity in the illustration. It is expressly contemplated that the teachings herein can also be applied with respect to the diagonal bipoles.

Any bipole can, in turn, be used to generate a bipolar electrogram according to techniques that will be familiar to those of ordinary skill in the art. Moreover, these bipolar electrograms can be combined (e.g., linearly combined) to generate electrograms, again including activation timing information, in any direction of the plane of catheter 13 by computing an E-field loop for a clique of electrodes. U.S. application Ser. No. 15/953,155, which is hereby incorporated by reference as though fully set forth herein, discloses details of computing an E-field loop for a clique of electrodes on a HD grid catheter.

In any event, catheter 13 can be used to simultaneously collect a plurality of electrophysiology data points for the various bipoles defined by electrodes 17 thereon, with each such electrophysiology data point including both localization information (e.g., position and orientation of a selected bipole) and an electrogram signal for the selected bipole. For purposes of illustration, methods according to the instant disclosure will be described with reference to a single electrophysiology data point, with a single bipolar electrogram, collected by catheter 13. It should be understood, however, that the teachings herein can be applied, in serial and/or in parallel, to multiple electrophysiology data points, and their respective electrograms (which may be bipolar or unipolar), collected by catheter 13.

In block 304, system 8 receives a definition of a window of interest within the electrogram signal and a window of exclusion within the electrogram signal. The window of exclusion is defined to facilitate the exclusion of undesired electrophysiology data points (e.g., points collected in the ventricle) from the anatomical map being generated.

Figure 5A:
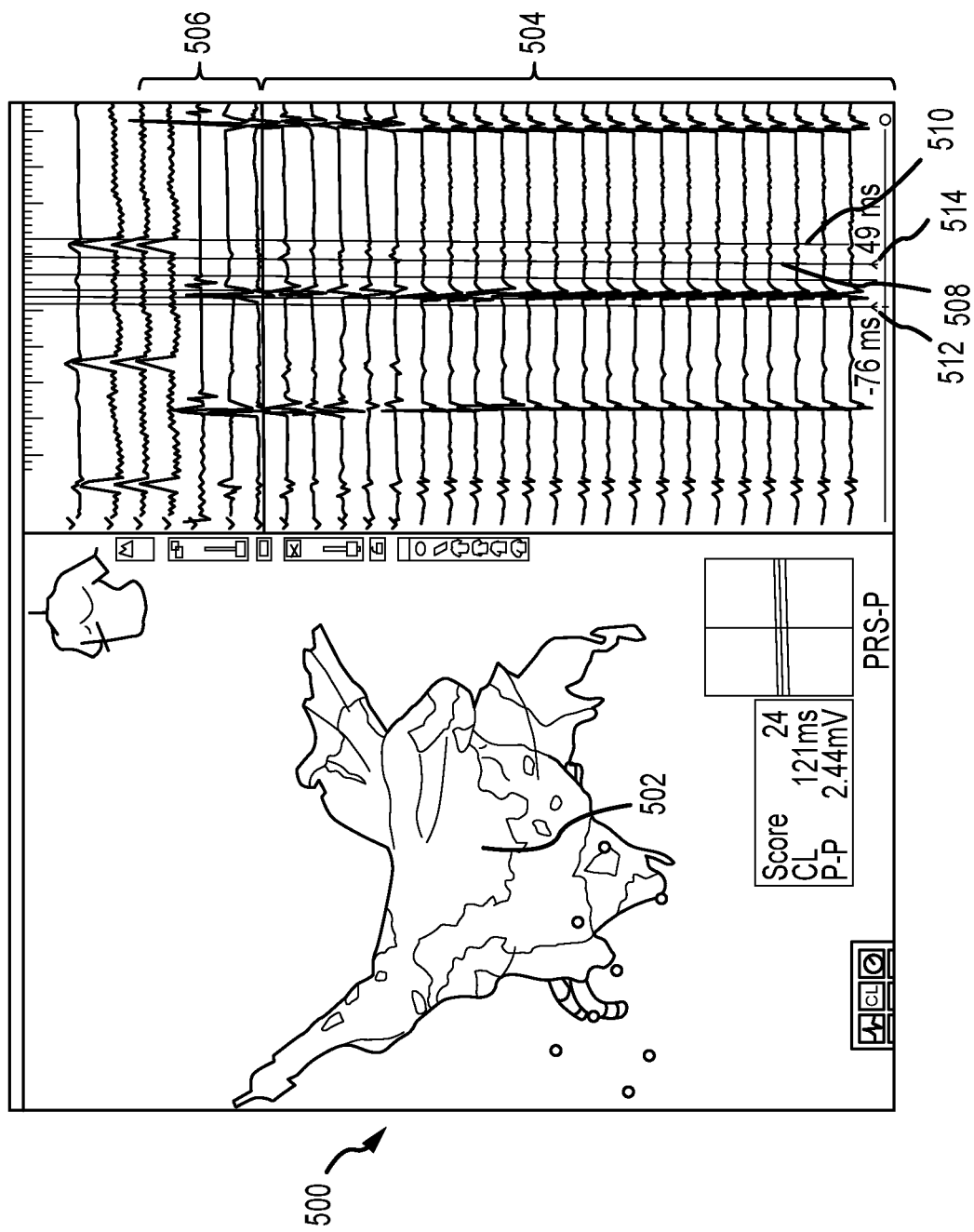
FIGS. 5A and 5B illustrate windows of exclusion and windows of interest according to aspects of the instant teachings.

The definition of a window of exclusion can be understood with reference to FIG. 5A, which is a representative output 500 from system 8 during an electrophysiology study as it may appear on display 23. Output 500 includes both a graphical representation of an electrophysiology map 502 and a plurality of electrogram traces 504 corresponding to a plurality of bipoles defined by electrodes 17 on catheter 13. Output 500 also includes traces 506 from EKG leads 6.

For purposes of illustrating the definition of a window of exclusion in block 304, assume that a practitioner is performing an atrial mapping procedure and wishes to exclude from the atrial map electrophysiology data points collected from within the patient's ventricle. The practitioner may accordingly define the window of exclusion, such as by dragging left and right lines of demarcation 508, 510, such that they surround the QRS complex of electrogram traces 504.

The window of interest can also be referred to as the "roving activation interval" (or "RAI"), and can generally be understood as the currently collected "beat." FIG. 5A depicts the window of interest just to the left of the window of exclusion, defined by left and right carats 512, 514. It is contemplated that the practitioner can adjust or redefine the window of interest by dragging carats 512, 514 along electrogram traces 504.

System 8 determines whether an electrophysiology data point should be included in or excluded from an anatomical map by comparing the electrogram signal within the window of interest to the electrogram signal within the window of exclusion with respect to at least one signal parameter, such as maximum peak-to-peak voltage.

Thus, in decision block 306, system 8 analyzes whether the maximum peak-to-peak voltage of the electrogram signal within the window of interest is at least as large as the maximum peak-to-peak voltage of the electrogram signal within the window of exclusion. If so (the "YES" exit from decision block 306), then the electrophysiology data point under consideration can be added to the anatomical map in block 308.

If not (the "NO" exit from decision block 306), then it is possible that the electrophysiology data point under consideration was collected from the ventricle rather than the atrium. It is also possible, however, that it was collected in the atrium, but near a region of scar, block, or that otherwise exhibits low voltage.

Accordingly, in decision block 310, system 8 analyzes whether the maximum peak-to-peak voltage of the electrogram signal within the window of exclusion exceeds a preset (e.g., user defined) threshold voltage, such as about 0.5 mV. If not (the "NO" exit from decision block 310), then the electrophysiology data point under consideration can be added to the anatomical map in block 308. If so (the "YES" exit from decision block 310), then the electrophysiology data point under consideration can be rejected/excluded from the anatomical map in block 312.

Figure 5B:
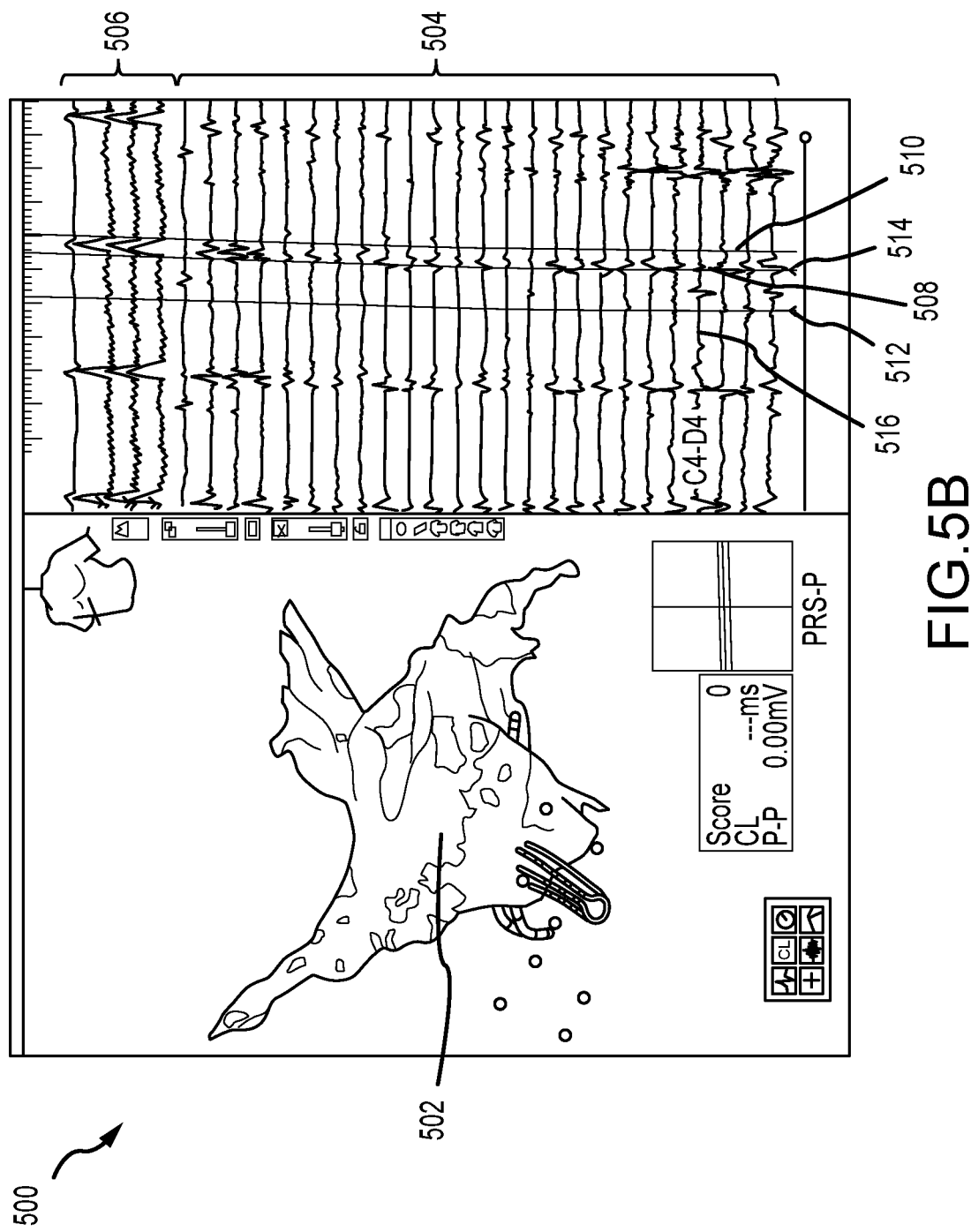

The process described above can be repeated for a plurality of electrophysiology data points, both collected sequentially (e.g., as catheter 13 moves through the patient's heart) and simultaneously (e.g., for multiple bipoles on catheter 13 for a single beat). Indeed, for simultaneously collected electrophysiology data points, the process described above can allow certain bipoles to be included and others to be excluded, such as if only a portion of catheter 13 is in the ventricle. In FIG. 5B, for instance, a portion of catheter 13 extends into the ventricle, and several electrogram traces 504 corresponding to bipoles within the ventricle exhibit higher maximum peak-to-peak voltages in the window of exclusion than the window of interest. Bipole C4-D4, however, corresponding to trace 516, remains within the atrium, and exhibits higher maximum peak-to-peak voltage in the window of interest than the window of exclusion. Accordingly, the electrophysiology data point corresponding to bipole C4-D4 will be added to the anatomical map, while the electrophysiology data points for all other bipoles may be excluded/rejected.

System 8 can also output a graphical representation of the anatomical map populated by the included electrophysiology data points (e.g., on display 23). As described above, the anatomical map can include a cardiac geometry and/or an electrophysiology map. Put another way, the teachings herein can be applied to generate the set of data points used to create a cardiac geometry model and/or the set of data points used to generate an electrophysiology map, which may in turn be output on a graphical representation of the cardiac geometry model.

Although several embodiments have been described above with a certain degree of particularity, those skilled in the art could make numerous alterations to the disclosed embodiments without departing from the spirit or scope of this invention.

For example, the teachings herein can be applied in real time (e.g., during an electrophysiology study) or during post-processing (e.g., to electrophysiology data points collected during an electrophysiology study performed at an earlier time).

As another example, different signal parameters, such as electrogram morphology, conduction velocity, local activation time, dV/dt, max peak positive, mean peak negative, and the like, can be used instead of or in addition to maximum peak-to-peak voltage to determine whether a given electrophysiology data point should be included or excluded/rejected. For instance, United States patent application publication no. 2015/0057507, which is hereby incorporated by reference as though fully set forth herein, describes the use of morphology matching scores (e.g., similarity values and/or correlation coefficients) to express the morphological similarity between two signals.

As yet another example, the teachings herein can be combined with the teachings of U.S. application Ser. No. 14/462,128 ("the '128 application"), which is hereby incorporated by reference as though fully set forth herein. When combined with the teachings of the '128 application, it may be computationally more efficient to apply the teachings of the '128 application to a collected electrophysiology data point before applying the instant teachings, but the opposite sequence would still be within the scope of the instant disclosure.

As a still further example, rather than discarding data points that are rejected/excluded at block 312, such points could instead be added to an alternative map (e.g., a ventricular geometry and/or electrophysiology map). In aspects of the disclosure, points that are rejected/excluded at block 312 may be added to such an alternative map if, and only if, they also satisfy one or more inclusion criteria (e.g., according to the teachings of the aforementioned '128 application).

All directional references (e.g., upper, lower, upward, downward, left, right, leftward, rightward, top, bottom, above, below, vertical, horizontal, clockwise, and counterclockwise) are only used for identification purposes to aid the reader's understanding of the present invention, and do not create limitations, particularly as to the position, orientation, or use of the invention. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other.

It is intended that all matter contained in the above description or shown in the accompanying drawings shall be interpreted as illustrative only and not limiting. Changes in detail or structure may be made without departing from the spirit of the invention as defined in the appended claims.

What is claimed is:

1. A method of generating a map of a portion of a patient's anatomy, comprising:
   receiving, at an electroanatomical mapping system, an electrophysiology data point, the electrophysiology data point including an electrogram signal;
   receiving, at the electroanatomical mapping system, a definition of a window of interest within the electrogram signal and a definition of a window of exclusion within the electrogram signal; and the electroanatomical mapping system adding the electrophysiology data point to the map of the portion of the patient's anatomy when a maximum peak-to-peak voltage of the electrogram signal within the window of interest exceeds a maximum peak-to-peak voltage of the electrogram signal within the window of exclusion.

2. The method according to claim 1, further comprising the electroanatomical mapping system adding the electrophysiology data point to the map of the portion of the patient's anatomy when:

the maximum peak-to-peak voltage of the electrogram signal within the window of interest does not exceed the maximum peak-to-peak voltage of the electrogram signal within the window of exclusion and the maximum peak-to-peak voltage of the electrogram signal within the window of exclusion does not exceed a preset threshold voltage.

3. The method according to claim 1, wherein the map of the portion of the patient's anatomy comprises an electrophysiology map.

4. The method according to claim 1, wherein the map of the portion of the patient's anatomy comprises a geometry.

5. The method according to claim 1, further comprising the electroanatomical mapping system outputting a graphical representation of the map of the portion of the patient's anatomy.

6. The method according to claim 1, wherein the window of exclusion comprises a QRS complex.

7. A method of generating a map of a portion of a patient's anatomy, comprising:

receiving, at the electroanatomical mapping system, an electrophysiology data point, the electrophysiology data point including an electrogram signal;

receiving, at an electroanatomical mapping system, a definition of a window of interest within the electrogram signal and a definition of a window of exclusion within the electrogram signal; and the electroanatomical mapping system adding the electrophysiology data point to the map of the portion of the patient's anatomy when a comparison of the window of interest to the window of exclusion with respect to at least one signal parameter satisfies at least one corresponding inclusion criterion.

8. The method according to claim 7, wherein the at least one signal parameter comprises maximum peak-to-peak voltage.

9. The method according to claim 8, wherein the at least one corresponding inclusion criterion comprises a maximum peak-to-peak voltage of the electrogram signal within the window of interest exceeding a maximum peak-to-peak voltage of the electrogram signal within the window of exclusion.

10. The method according to claim 8, wherein the at least one corresponding inclusion criterion comprises:

a maximum peak-to-peak voltage of the electrogram signal within the window of interest not exceeding a maximum peak-to-peak voltage of the electrogram signal within the window of exclusion; and the maximum peak-to-peak voltage of the electrogram signal within the window of exclusion interval not exceeding a preset threshold voltage.

11. The method according to claim 7, wherein the at least one signal parameter comprises electrogram morphology.

12. The method according to claim 7, wherein the at least one signal parameter comprises conduction velocity.

13. The method according to claim 7, further comprising the electroanatomical mapping system adding the electrophysiology data point to an alternative map of the portion of the patient's anatomy when the comparison of the window of interest to the window of exclusion with respect to the at least one signal parameter does not satisfy the at least one corresponding inclusion criterion.

14. An electroanatomical mapping system for generating a map of a portion of a patient's anatomy, comprising:

an inclusion processor configured to:

receive as input an electrophysiology data point including an electrogram signal;

receive as input a definition of a window of interest within the electrogram signal and a definition of a window of exclusion within the electrogram signal;

compare the window of interest to the window of exclusion with respect to at least one signal parameter; and add the electrophysiology data point to the map of the portion of the patient's anatomy when the comparison of the window of interest to the window of exclusion satisfies at least one corresponding inclusion criterion.

15. The system according to claim 14, further comprising a mapping processor configured to output a graphical representation of the map of the portion of the patient's anatomy.

16. The system according to claim 15, wherein the map of the portion of the patient's anatomy comprises a cardiac geometry.

17. The system according to claim 15, wherein the map of the portion of the patient's anatomy comprises an electrophysiology map.

18. The system according to claim 14, wherein the at least one signal parameter comprises maximum peak-to-peak voltage.

19. The system according to claim 18, wherein the at least one corresponding inclusion criterion comprises a maximum peak-to-peak voltage of the electrogram signal within the window of interest exceeding a maximum peak-to-peak voltage of the electrogram signal within the window of exclusion.

20. The system according to claim 18, wherein the at least one corresponding inclusion criterion comprises:

a maximum peak-to-peak voltage of the electrogram signal within the window of interest not exceeding a maximum peak-to-peak voltage of the electrogram signal within the window of exclusion; and the maximum peak-to-peak voltage of the electrogram signal within the window of exclusion interval not exceeding a preset threshold voltage.

* * * * *